(12) United States Patent
Brody

(10) Patent No.: US 11,511,074 B2
(45) Date of Patent: Nov. 29, 2022

(54) URODYNAMIC INVESTIGATION APPARATUS, SYSTEM, AND METHODS

(71) Applicant: SRS Medical Systems, LLC, North Billerica, MA (US)

(72) Inventor: Lee Brody, Somerville, MA (US)

(73) Assignee: SRS Medical Systems, LLC, North Billerica, MA (US)

( * ) Notice: Subject to any disclaimer, the term of this patent is extended or adjusted under 35 U.S.C. 154(b) by 827 days.

(21) Appl. No.: 16/451,129

(22) Filed: Jun. 25, 2019

(65) Prior Publication Data

US 2020/0038629 A1     Feb. 6, 2020

Related U.S. Application Data

(63) Continuation of application No. PCT/US2019/017621, filed on Feb. 12, 2019.
(Continued)

(51) Int. Cl.
*A61M 25/00* (2006.01)
*A61B 5/20* (2006.01)
(Continued)

(52) U.S. Cl.
CPC ......... *A61M 25/0041* (2013.01); *A61B 5/205* (2013.01); *A61B 5/208* (2013.01);
(Continued)

(58) Field of Classification Search
CPC .......... A61M 25/0041; A61M 25/0017; A61M 2025/0001; A61M 2205/3331;
(Continued)

(56) References Cited

U.S. PATENT DOCUMENTS 2,982,511 A     2/1959  Connor
3,570,488 A *   3/1971  Diskin ................ A61M 3/0208
                                                  604/245
(Continued)

FOREIGN PATENT DOCUMENTS

DE         3236249         4/1984
EP         0097521 A1      1/1984
(Continued)

OTHER PUBLICATIONS

International Search Report and Written Opinion from PCT/US2019/017621; 13 pages; Shane Thomas; dated Apr. 30, 2019.
(Continued)

*Primary Examiner* — Adam Marcetich
(74) *Attorney, Agent, or Firm* — Dicke, Billig & Czaja, PLLC

(57) ABSTRACT

A urodynamic investigation apparatus for receipt of urine from a bladder is provided. The apparatus is characterized by a tubular element, first and second fittings, and a sleeve element, for select passage of urine there through, within the tubular element. The tubular element is characterized by opposing first and second end portions, and a port. The fittings are adapted to be received by the opposing end portions of the tubular element so as to delimit an apparatus chamber. The sleeve element, suspended between the fittings within the chamber, has collapsed and open configurations. The collapsed configuration is indicative of a no urine flow condition, and the open configuration indicative of a urine flow condition, with the sleeve element urine flow condition being a function of pressure applied to the chamber via the port of the tubular element.

28 Claims, 16 Drawing Sheets

Related U.S. Application Data

(60) Provisional application No. 62/742,602, filed on Oct. 8, 2018, provisional application No. 62/633,652, filed on Feb. 22, 2018.

(51) Int. Cl.
*A61B 5/389* (2021.01)
*A61F 5/453* (2006.01)

(52) U.S. Cl.
CPC ...... *A61B 5/389* (2021.01); *A61B 2562/0247* (2013.01); *A61F 5/453* (2013.01); *A61M 25/0017* (2013.01); *A61M 2025/0001* (2013.01); *A61M 2205/3331* (2013.01); *A61M 2210/1096* (2013.01)

(58) Field of Classification Search
CPC ........... A61M 2210/1096; A61B 5/205; A61B 5/208; A61B 5/389; A61B 2562/0247; A61B 5/391; A61B 2018/00505; A61B 2018/00511; A61B 2018/00517; A61B 2018/00523; A61B 5/202; A61B 5/204; A61B 5/207; A61F 5/453
See application file for complete search history.

(56) References Cited

U.S. PATENT DOCUMENTS

| | | | |
|---|---|---|---|
| 4,099,412 | A | 7/1978 | Nehrbass |
| 4,195,810 | A | 4/1980 | Lavin |
| 4,701,160 | A | 10/1987 | Lindsay et al. |
| 4,766,931 | A | 8/1988 | Chauvier et al. |
| 5,161,773 | A | 11/1992 | Tower |
| 5,176,630 | A | 1/1993 | Shilling |
| 5,186,431 | A | 2/1993 | Tamari |
| 5,190,534 | A | 3/1993 | Kendell |
| 5,205,325 | A | 4/1993 | Piper |
| 5,305,983 | A | 4/1994 | Haase et al. |
| 5,336,051 | A | 8/1994 | Tamari |
| 5,377,101 | A * | 12/1994 | Rollema ............... G16H 10/40 422/68.1 |
| 5,405,319 | A | 4/1995 | Abell |
| 5,634,878 | A | 6/1997 | Grundei et al. |
| 5,823,972 | A | 10/1998 | McRae |
| 5,897,533 | A | 4/1999 | Glickman |
| 6,070,553 | A | 6/2000 | Bucker |
| 6,138,984 | A | 10/2000 | Abell |
| 6,386,596 | B1 | 5/2002 | Olson |
| 6,506,169 | B2 | 1/2003 | Griffiths |
| 7,118,086 | B1 | 10/2006 | Borglum et al. |
| 7,662,146 | B2 | 2/2010 | House |
| 7,789,873 | B2 | 9/2010 | Kubalak et al. |
| 9,101,314 | B2 | 8/2015 | Shi |
| 9,277,884 | B2 | 3/2016 | Kron et al. |
| 2001/0020162 | A1 * | 9/2001 | Mosel ................... A61B 5/202 604/66 |
| 2002/0010404 | A1 * | 1/2002 | Griffiths ................ A61B 5/205 600/587 |
| 2003/0047128 | A1 | 3/2003 | Delp |
| 2004/0044307 | A1 | 3/2004 | Richardson et al. |
| 2004/0172008 | A1 | 9/2004 | Layer |
| 2004/0260163 | A1 | 12/2004 | Kron et al. |
| 2005/0045480 | A1 | 3/2005 | Krumme |
| 2005/0256447 | A1 | 11/2005 | Richardson et al. |
| 2006/0009732 | A1 | 1/2006 | Hardy |
| 2006/0241509 | A1 * | 10/2006 | Badr ..................... A61B 5/085 600/533 |
| 2008/0027373 | A1 * | 1/2008 | Holte ....................... G01L 7/20 604/27 |
| 2008/0083889 | A1 | 4/2008 | Raftis |
| 2008/0172041 | A1 * | 7/2008 | Shehata ................. A61M 25/04 604/544 |
| 2008/0275366 | A1 * | 11/2008 | Brohan ................. A61B 5/208 600/584 |
| 2011/0186757 | A1 | 8/2011 | Kawamura et al. |
| 2012/0132284 | A1 | 5/2012 | Buhler |
| 2014/0090644 | A1 | 4/2014 | Aldana |
| 2014/0200482 | A1 * | 7/2014 | Shi ......................... A61B 5/036 600/561 |
| 2017/0055874 | A1 | 3/2017 | Papirov et al. |
| 2017/0055983 | A1 | 3/2017 | Bracy |
| 2017/0319086 | A1 | 11/2017 | Masuda et al. |
| 2017/0350529 | A1 | 12/2017 | Vargas Fonseca |
| 2018/0070802 | A1 | 3/2018 | Becerra et al. |
| 2019/0076180 | A1 * | 3/2019 | Franco .................. A61B 5/205 |
| 2019/0216401 | A1 * | 7/2019 | Brody ............. A61M 25/10185 |
| 2019/0350511 | A1 * | 11/2019 | Franco ................... A61B 5/20 |
| 2020/0069856 | A1 | 3/2020 | Chapman et al. |

FOREIGN PATENT DOCUMENTS

| | | |
|---|---|---|
| EP | 2762176 B1 | 11/2016 |
| GB | 1432833 | 4/1976 |
| WO | 2012154742 A1 | 11/2012 |
| WO | 2016183083 A1 | 11/2016 |
| WO | 2017087182 A1 | 5/2017 |

OTHER PUBLICATIONS

D'Ancona et al. "New Method for Minimally Invasive Urodynamic Assesment in Men with Lower Urinary Tract Symptoms", Urology, Belle Mead, NJ, US, vol. 71, No. 1, Jan. 30, 2008, pp. 75-78.

Partial Supplementary European Search Report for EP19757898.2, dated Oct. 6, 2021, 17 pages, Jan Knoop.

* cited by examiner

URODYNAMIC INVESTIGATION APPARATUS, SYSTEM, AND METHODS

This utility patent application filed pursuant to 35 U.S.C. § 111(a) and 37 CFR § 1.53(b) (1) is a bypass continuation of application Ser. No. PCT/US2019/017621, filed Feb. 12, 2019, with priority claim thereto under 35 U.S.C. § 120, which is an international patent application filed under 35 U.S.C. § 363 claiming priority under 35 U.S.C. § 120 to U.S. Pat. Appl. Ser. No. 62/633,652 filed Feb. 22, 2018 and to U.S. Pat. Appl. Ser. No. 62/742,602 filed Oct. 8, 2018, each filed pursuant to 35 U.S.C. § 111(b) and entitled PULSING URETHRAL COMPRESSION AND ABDOMINAL EMG FOR BPH DIAGNOSIS, the disclosures of which are hereby incorporated by reference in their entireties.

TECHNICAL FIELD

The present invention is generally directed to urodynamic investigations on male subjects, more particularly, to improvements relative to non-invasive urodynamic investigations as shown and described, for example, in U.S. Pat. No. 6,506,169 (Griffiths), incorporated herein by reference in its entirety, including attendant urodynamic investigation devices, apparatus, assemblies or subassemblies, and/or methods as the case may be.

BACKGROUND

In relation to urodynamic investigations, a Voiding Pressure Study (VPS) is the diagnostic gold-standard for determining the relationship between pressures generated by the body, and the urine output flow rate. By simultaneously determining the pressures generated by the body during voiding and the resulting urine output (i.e., discharge) flow rate, a healthcare provider, commonly a urologist, can deduce the amount of outlet flow resistance at the bladder neck and urethra. This information, in combination, can inform as to the potential sources of lower urinary tract symptoms, and the likelihood that certain interventions will be successful. For instance, if it is determined that a subject generates high pressures with a low urine output flow, he is deduced to have high outlet resistance, and a procedure to lower the outlet resistance may be considered.

Traditional VPS involve the simultaneous measurement of three physiologic parameters or signals: (1) a measurement catheter is placed in the bladder which continuously measures the vesical pressure within the bladder; (2) a measurement catheter is placed in the abdominal cavity which continuously measures abdominal pressure; and, (3) the voided volume of urine is collected and continuously weighed so that urine flow rate can be ascertained.

The body generates pressure to force urine out of the body from two sources: (1) the primary source should be a coordinated contraction of the bladder wall (i.e., detrusor muscle), and (2) some subjects "bear down" and voluntarily produce an abdominal contraction. The measurement catheter in the bladder cannot differentiate the pressure generated by the detrusor muscle from that generated by the abdomen contraction. In order to isolate (i.e., identify) the pressure generated by the detrusor, the abdominal pressure must be subtracted from the vesical pressure.

An exemplary pressure versus time relationship during a void is illustrated in FIG. 1, namely, the top (uppermost) graph is the output of the pressure sensor in the bladder (Pves—vesical pressure), the middle (intermediate) graph is the output of the pressure sensor in the abdominal cavity (Pabd—abdominal pressure) and the bottom (lowermost) graph is the calculated difference resultant (Pves—Pabd), namely, the amount of pressure generated by the bladder walls contracting (Pdet—detrusor pressure). The depicted relationships of FIG. 1 indicate a subject who is generating substantial pressure during a void, however, nearly all of the pressure generated is coming from an abdominal contraction.

Traditional VPS is an underutilized diagnostic in the U.S. for subjects suspected of having bladder outlet obstruction. The test is an invasive test that requires catheters to be placed into and through both the tip of the penis and the rectum, and it involves filling the bladder with sterile water. It is estimated that less than 1% of patients being treated for bladder outlet obstruction receive a traditional VPS.

Applicant SRS Medical Systems, LLC (Massachusetts, USA) manufactures the CT3000 Plus Complete Urodynamics System, a system characterized by a UroCuff® bladder function monitoring/assessment device. The device and system enable a non-invasive voiding pressure study called the UroCuff bladder function test which simultaneously measures urine flow rate and vesical pressure (see "Principles of the UroCuff Test," SRS Medical Systems, Inc., adopted from Dr. Michael Drinnan & Dr. Clive Griffiths (Newcastle University), P/N 291-045 Rev A, incorporated herein by reference in its entirety). With reference to FIG. 2, the study/study system 21 contemplates controlled regulated pressure application to a pneumatic penile cuff 23, via an automated pressure supply apparatus or system 25, during a urine void event, with urine egress monitoring/collection for the sake of direct or indicted volumetric flow rate determination, via a urine collection/flow rate indicating or determining system 27, during select pressure application.

After having naturally filled his bladder by drinking fluids so as to attain a comfortably full bladder, the subject is positioned for the test. Vesical pressure is measured non-invasively with the pneumatic penile cuff (i.e., an article resembling a blood pressure cuff) instead of via an indwelling catheter.

The principle of the test is similar to blood pressure measurement. When the subject is ready to void, the cuff is fitted around the penis, and the subject is asked to void, directly or otherwise, into a flow measuring device, apparatus or system. When voiding has commenced, the cuff is inflated with aid of the automatic pressure supply and control assembly/subassembly until the urine discharge stream is interrupted via application of the applied cuff restriction. Further inflation cycles are executed until the void is complete. The cuff pressure required to interrupt flow equals vesical pressure at the time of interruption.

Once the test is complete, pressure-flow data is generated as a modified nomogram in a characteristic UroCuff bladder function test report. Nomograms from two different subjects having identical maximum flow rates of 3.1 ml/s are illustrated in FIG. 3, each of these subjects presenting as "low flow rate" subjects, however, the UroCuff bladder function test nomogram on the left reveals that the first subject (A) has a high vesical pressure (~173 cmH$_2$O), while the nomogram on the right reveals the second subject (B) has low vesical pressure (~61 cmH$_2$O). The first subject is more likely to have voiding symptom improvement as a result of a de-obstructive procedure.

The current UroCuff protocol involves waiting for the subject to begin voiding. Once the subject voids, the cuff inflates at a linear rate of 10 cmH$_2$O per second. The urine flow rate is constantly measured as the cuff inflates, and the protocol requires the cuff to inflate to a pressure that interrupts the flow of urine. Once the flow of urine is interrupted, the cuff completely deflates and a second inflation cycle is started. The second inflation cycle again linearly increases the pressure in the cuff until the urine flow is completely interrupted. Cycles repeat until the subject has emptied his bladder so as to conclude the void and thus complete the test.

An illustrative graphic showing parameter values as a function of time is provided herein FIG. 4 indicating performance of four inflation cycles with the monitoring and recording of applied pressure, urine discharge flow rate, and urine discharge volume. The top (uppermost) graph shows the cuff pressure and a series of four linear inflations (i.e., linear pressure increases to the point of discharge cessation/stoppage), with the middle (intermediate) graph showing the urine flow rate. Comparison of the depicted relationships indicates that as the cuff pressure increases, the urine flow rate decreases. The bottom (lowermost) graph shows the total voided volume of urine.

An analysis of the four inflations from the FIG. 4 study is illustrated in the graphs of FIG. 5. Each inflation event or sequence is transformed into a flow versus cuff pressure graph, and an analysis is performed to determine the pressure applied by the cuff which caused an interruption of the urine flow. This is known as the interruption pressure. In this example, inflation #2 resulted in the maximum interruption pressure of 125 $cmH_2O$, which is the data point utilized to represent the vesical pressure.

There are three shortcomings or at least challenges associated with the current UroCuff bladder function protocol: (1) more often than not, a subject experiences discomfort by having the cuff inflate to a pressure which cuts of urine flow (i.e., application of an interruption pressure is at least uncomfortable, and at most painful); (2) if a subject has limited voiding volume, the protocol may only involve one or two inflation cycles which correspondingly limits data/measurement accuracy and associated assessment; and, (3) some subjects instinctively create abdominal pressure by pushing at the end of a void, and this phenomenon makes it difficult to determine the interrupt pressure.

Applicant's present work contemplates three distinct improvements to the known UroCuff bladder function test. First, an alternate cuff inflation/deflation approach is provided, namely one that is characterized by a less is more data acquisition approach. Second, supplemental data acquisition via the use of abdominal electromyography (EMG) provides for an improved estimation of Pdet and Pabd. Third, circumscribing the penis with a pneumatic cuff in furtherance of data acquisition is eliminated with placement of a pneumatic cuff substitute assembly distal to the urethra for, among other things, improved, reliable data acquisition, provided.

SUMMARY OF THE INVENTION

A urodynamic investigation apparatus for receipt of urine from a bladder is provided. The apparatus is characterized by a tubular element, first and second fittings, and a sleeve element, for select passage of urine there through, within the tubular element. The tubular element is characterized by opposing first and second end portions, and a port. The fittings are adapted to be received by the opposing end portions of the tubular element so as to delimit an apparatus chamber. The sleeve element, suspended between the fittings within the chamber, has collapsed and open configurations. The collapsed configuration is indicative of a no urine flow condition, and the open configuration indicative of a urine flow condition, with the sleeve element urine flow condition being a function of pressure applied to the chamber via the port of the tubular element.

A fitting of the fittings may be configured to receive a drainage tube of an external catheter, or alternately configured to receive or cooperatively engage periurethral tissue. Moreover, a fitting of the fittings may be configured or adapted to operatively unite with downstream test components, such as, without limitation, a urine egress routing tube, or urine flowrate determination apparatus. Further still, an interface of, for, or between the fittings and the tubular element is characterized by a leak proof seal, or in one embodiment, an O-ring or the like.

The sleeve element may be directly or indirectly suspended in relation to the fixtures. Anchor elements are contemplated but are not required. Advantageously, the sleeve element is a compliant element, comprised of, for example and without limitation, a thermoplastic, more particularly and advantageously, a shrink tubing.

In addition to the urodynamic investigation apparatus, improved and enhanced test protocols are contemplated. A contemplated improved urodynamic pressure profiling method is characterized by applying and recording a first pressure to a lumen carrying urine discharge from a bladder without terminating urine flow through the lumen and determining a urine flow rate corresponding to the first applied pressure. Thereafter, a second pressure is applied to the lumen carrying urine discharge from the bladder, without terminating urine flow there through, and recorded, the second pressure greater or less than the first pressure by a select pressure increment. The urine flow rate corresponding to the second applied pressure is likewise determined. Next, a third pressure is advantageously applied to the lumen carrying urine discharge from the bladder, without terminating urine flow there through, and recorded, the third pressure greater or less than the second pressure by the select pressure increment. The urine flow rate corresponding to the third applied pressure is likewise determined. Finally, via an assessment of applied pressures and corresponding flow rates, either or both of an applied pressure corresponding to a no flow urine condition and maximum urine discharge flow rate is ascertained.

Finally, an enhanced urodynamic pressure profiling method is characterized by applying and recording a first pressure to a lumen carrying urine discharge from a bladder without terminating urine flow through the lumen and determining a urine flow rate corresponding to the first applied pressure. Simultaneously therewith, surface electrodes, part-and-parcel of an EMG apparatus/system, are positioned and applied to an abdomen of a subject, with a voltage selectively applied to the surface electrodes while recording the applied voltage and detected voltage generated by the active abdominal muscles. More specific features and advantages obtained in view of the summarized features will become apparent with reference to the drawing figures and DETAILED DESCRIPTION OF THE INVENTION.

BRIEF DESCRIPTION OF THE DRAWINGS

All figures have been prepared, and are included to facilitate and/or enhance an understanding of the basic teachings of the contemplated embodiments, and/or the concepts underlying same, and are incorporated in and constitute a part of this specification. While the drawings illustrate embodiments and context with respect thereto, and together with the description serve to explain principles of embodiments, other embodiments and many of the intended advantages of the disclosed systems, subsystems, assemblies, subassemblies, apparatus, devices, mechanisms, methods, etc. will be readily appreciated as they become better understood by reference to the following detailed description and figures. It is to be noted that the elements of the drawings are not necessarily to scale relative to each other, with like reference numerals designating corresponding similar parts/structures.

FIGS. 1-15 are provided herewith wherein:

FIG. 1 depicts illustrative voiding pressure study pressure component values as a function of subject void time, namely, vesical, abdominal, and detrusor pressure components;

FIG. 2 schematically depicts a known voiding pressure study procedure, more particularly, a UroCuff® bladder function monitoring/assessment procedure;

FIG. 4 depicts exemplary applied pressure (upper), urine discharge flow rate (intermediate), and urine discharge volume (lower) values as a function of test/cycle time for the FIG. 2 procedure, four pressure cycle applications indicated;

FIG. 5 depicts relationships for and between urine discharge flow rate and applied pressure for/at each pressure cycle application event of FIG. 4;

FIG. 6 depicts the relationships of FIG. 5 wherein data sets acquired via an improved bladder function test procedure are illustrated/superimposed thereon demonstrating the predictive value of the improved procedure;

FIG. 7 schematically depicts an improved voiding pressure study procedure, more particularly, a bladder function monitoring/assessment procedure characterized by a urodynamic investigation apparatus in lieu of a penile cuff characteristic of the UroCuff bladder function test;

FIG. 8 depicts, side elevation view, a contemplated urodynamic investigation apparatus for receipt of urine from the bladder;

FIG. 9 depicts, top plan view, the apparatus of FIG. 8;

FIG. 10 depicts, elevation sectional view, the apparatus of FIG. 8;

FIG. 11 depicts, exploded isometric view, the apparatus of FIG. 8;

FIG. 12 depicts, side elevation view, a further contemplated urodynamic investigation apparatus for receipt of urine from the bladder;

FIG. 13 depicts, top plan view, the apparatus of FIG. 12;

FIG. 14 depicts, elevation sectional view, the apparatus of FIG. 12; and,

FIG. 15 depicts, exploded isometric view, the apparatus of FIG. 12.

DETAILED DESCRIPTION OF THE INVENTION

In advance of particulars of and for improved urodynamic pressure profiling methodologies on the one hand, and of and for improved non-invasive voiding pressure study procedures characterized by a urodynamic investigation apparatus for the receipt of urine from the bladder on the other hand, an overview the instant description is believed worthwhile. Moreover, preliminary remarks will thereafter follow to better inform disclosure particulars.

Figure 6:
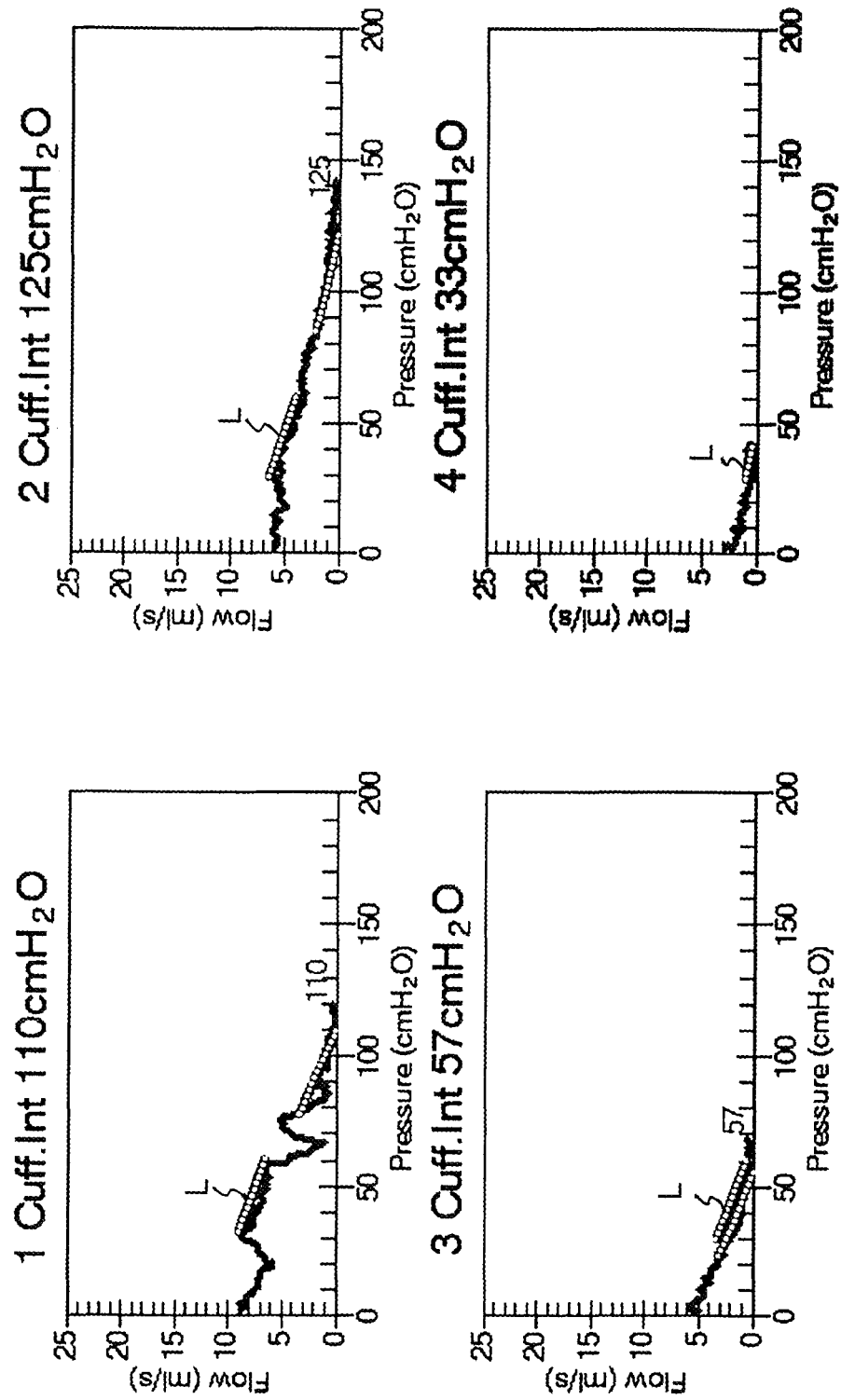

As to organization, the description proceeds with a discussion of one or more high value data acquisition approaches characteristic of the one or more contemplated improved and/or enhanced urodynamic pressure profiling methodologies, e.g., with initial reference to FIG. 6. Thereafter, and notionally, the contemplated improved and advantageous voiding pressure study procedure/set-up (FIG. 7), and contemplated, non-limiting advantageous urodynamic investigation apparatus embodiments (FIG. 8 et seq. & FIG. 12 et seq.) are presented.

Notionally, Applicant aims not to abandon the well-known and widely practiced UroCuff bladder function test, but to instead offer purposeful, advantageous enhancements, adaptations, substitutions, etc. in either or both of the protocol (i.e., the methodology) and the test set up, system, apparatus, etc. Moreover, while particulars are presented in the context of the UroCuff test, contemplated improvements need not be so limited, with implementation of disclosed methodologies/apparatuses readily suited, with minimal or no adaptation, to/for heretofore known and emerging VPS approaches/protocols.

A first contemplated alternate approach to known bladder function test protocols implicates, and is directed to, pressure profiling, more particularly, to an advantageous departure in the manner in which the inflations/deflations occur. Specifically, rather than performing a series of inflations (i.e., pressure applications) which culminate in the interruption (i.e., stoppage) of urine discharge flow, each of which is followed by deflation (i.e., a reverse of the pressure application), one or more inflation sequences can occur in which the applied pressure increases and decreases to establish a relationship between pressure and flow without resort to a cessation of urine discharge flow which often times, with use of a penile cuff, can be an issue for the test subject and which is likewise known to skew data sets. Via the instant approach, namely, limiting pressure application to a subset of the pressure range delimited by at least the interrupt pressure, and extrapolating the obtained data sets to ascertain the interruption pressure and maximum urine flow rate, rather than repeatedly measuring it, an improved subject experience is had, with arguably "better" data obtained (i.e., at least as good data obtained) in what is a shortened period for data acquisition.

For instance, and without limitation, applied pressure (e.g., cuff pressure) may be linearly increased, and linearly decreased at 10 cmH$_2$O/s. The subject could begin laminar flow, and once flow commences, applied pressure could increase to a maximum, for example 60 cmH$_2$O. Upon registering an applied pressure of 60 cmH$_2$O, the cuff could linearly deflate to a minimum pressure, for example 30 cmH$_2$O. This abbreviated inflation/deflation cycle could continue to repeat until the subject completes the void.

Generally, and without limitation, the contemplated improved urodynamic pressure profiling method is characterized by applying and recording a first pressure to a lumen carrying urine discharge from a bladder without terminating urine flow through the lumen and determining a urine flow rate corresponding to the first applied pressure. Thereafter, a second pressure is applied to the lumen carrying urine discharge from the bladder, without terminating urine flow there through, and recorded, the second pressure greater or less than the first pressure by a select pressure increment. The urine flow rate corresponding to the second applied pressure is likewise determined. Next, but not necessarily, a third pressure is applied to the lumen carrying urine discharge from the bladder, without terminating urine flow there through, and recorded, the third pressure greater or less than the second pressure by the select pressure increment. The urine flow rate corresponding to the third applied pressure is likewise determined. Finally, via an assessment of applied pressures and corresponding flow rates, either or both of an applied pressure corresponding to a no flow urine condition and maximum urine discharge flow rate is ascertained.

Figure 5:
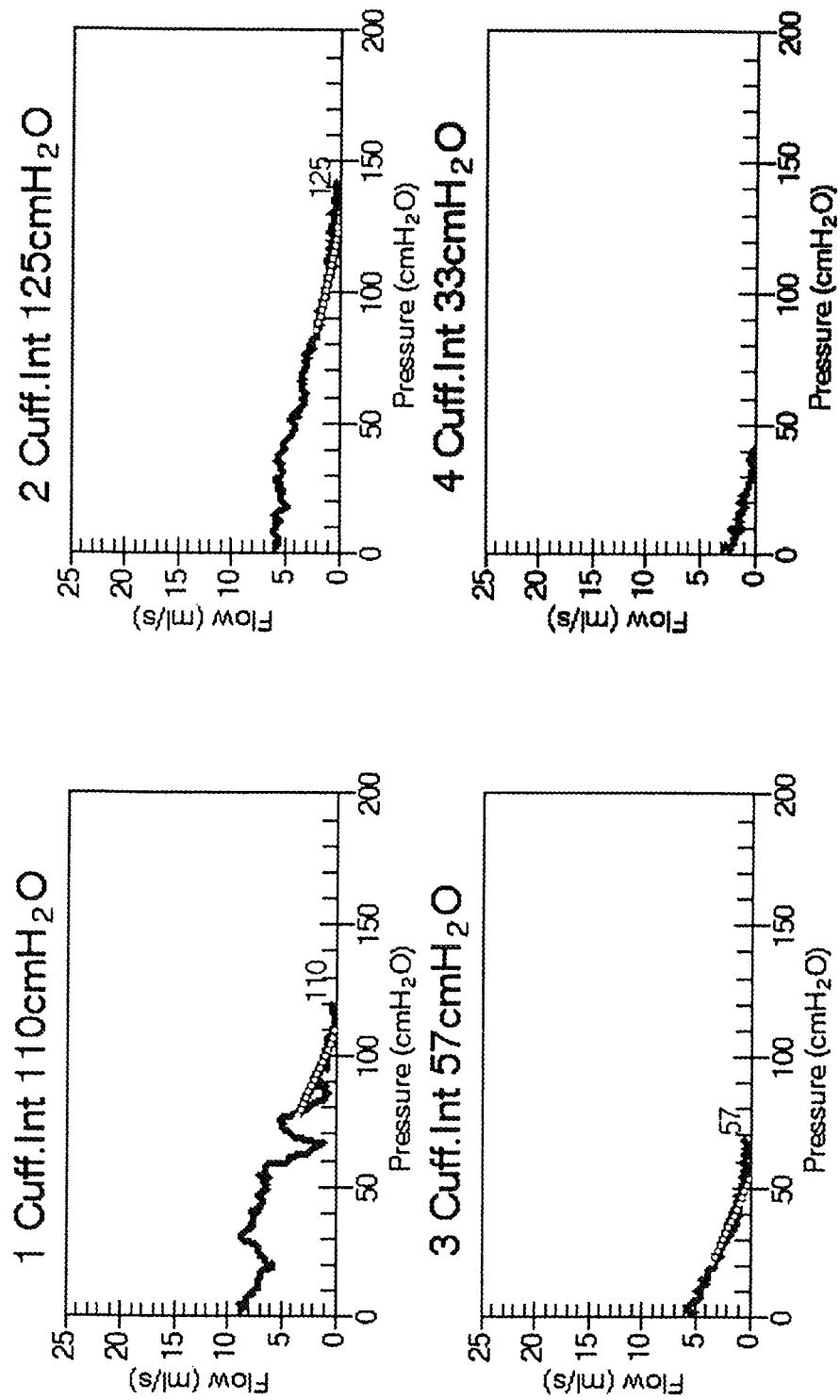

The predictive value of the described protocol/method is best appreciated with reference to FIG. 6 wherein the inflation analysis of FIG. 5 is represented with a line (L) on each inflation sequence representing the analysis of the pressure-flow relationship between 30-60 cmH$_2$O. It is readily observable that these data could be extrapolated to reliably predict interrupt pressure and maximum flow rate without resort to/for direct measurement.

A second contemplated alternate or supplemental approach to known bladder function test protocols implicates, and is directed to, improved or enhanced accuracy, more particularly, to supplementing the heretofore practiced UroCuff test with abdominal electromyography (EMG) data acquisition and assessment so as to estimate Pdet and Pabd pressure components. The UroCuff Test currently reports the interrupt pressure, which is the pressure that the cuff applies to the penile urethra to interrupt urine flow. Moreover, the relationship between cuff pressure and urine flow rate is continuously monitored, with such approach permitting an understanding of how increased outlet resistance affects flow rate, and thus allows characterization of the pressure within the bladder (i.e., vesical pressure).

Via additionally simultaneously measuring surface EMG on the abdomen of a test subject, an accurate determination of whether the subject abdominally strains during the voiding phase of the study is possible. An improved or enhanced UroCuff bladder function test protocol can be created in which one or more surface EMG sensors can be placed on the abdomen for simultaneous sensing and recording during the voiding study.

Generally, and without limitation, the contemplated enhanced urodynamic pressure profiling method is characterized by applying and recording a first pressure to a lumen carrying urine discharge from a bladder without terminating urine flow through the lumen and determining a urine flow rate corresponding to the first applied pressure. Simultaneously therewith, surface electrodes, part-and-parcel of an EMG apparatus/system, are positioned and applied to an abdomen of a subject, with a voltage selectively applied to the surface electrodes while recording the applied voltage and detected voltage generated by the active abdominal muscles. The combination of these steps may be repeated in the context of the traditional UroCuff bladder function test, or, for instance, in the context of the previously described improved urodynamic pressure profiling method.

Figure 1:
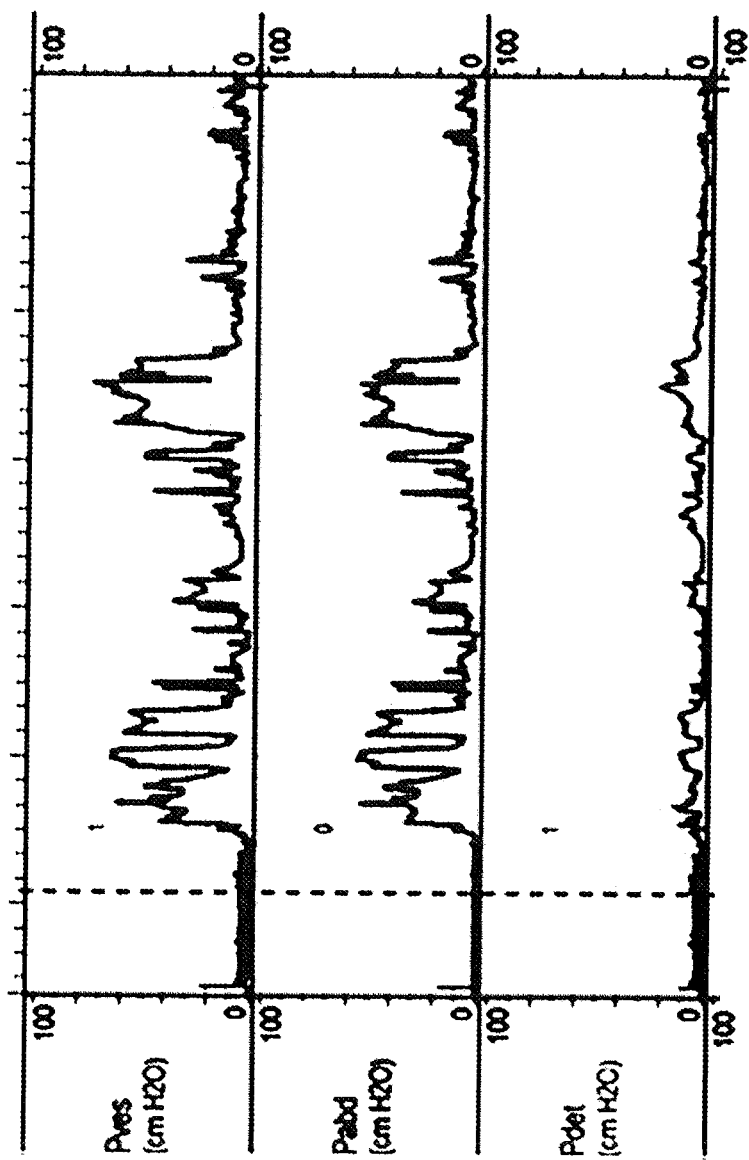
Figure 2:
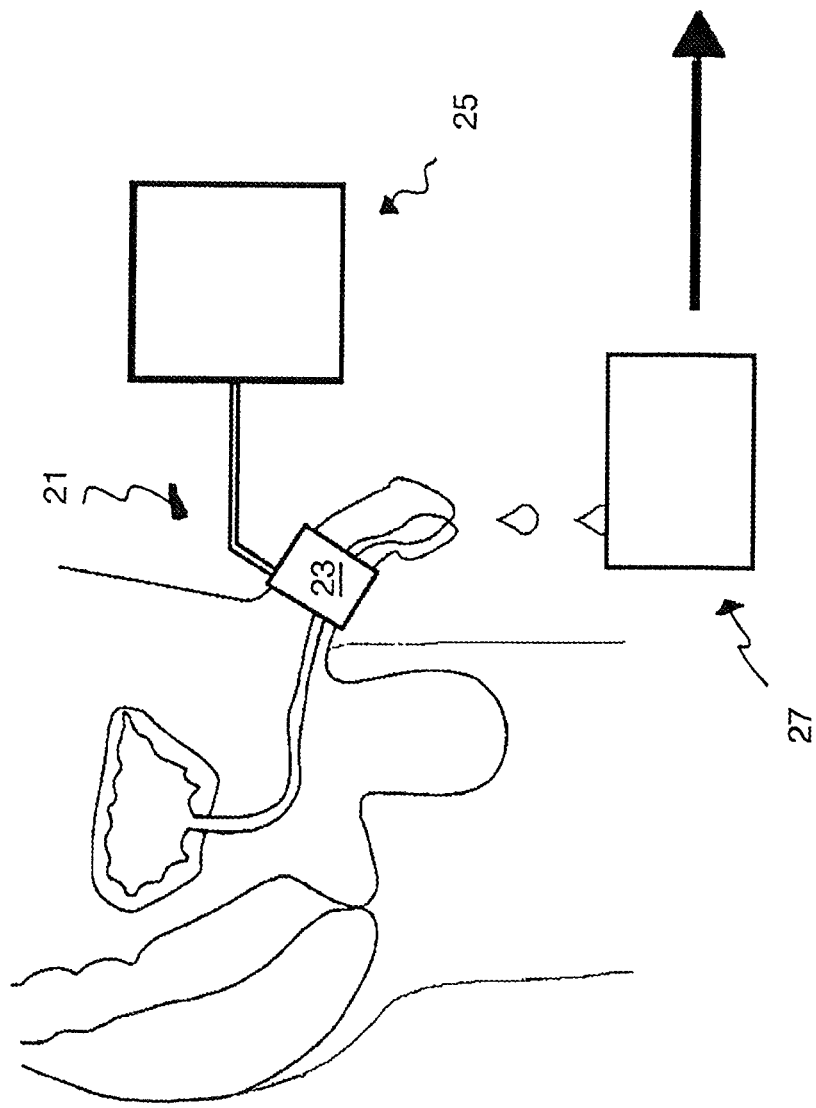
Figure 3A:
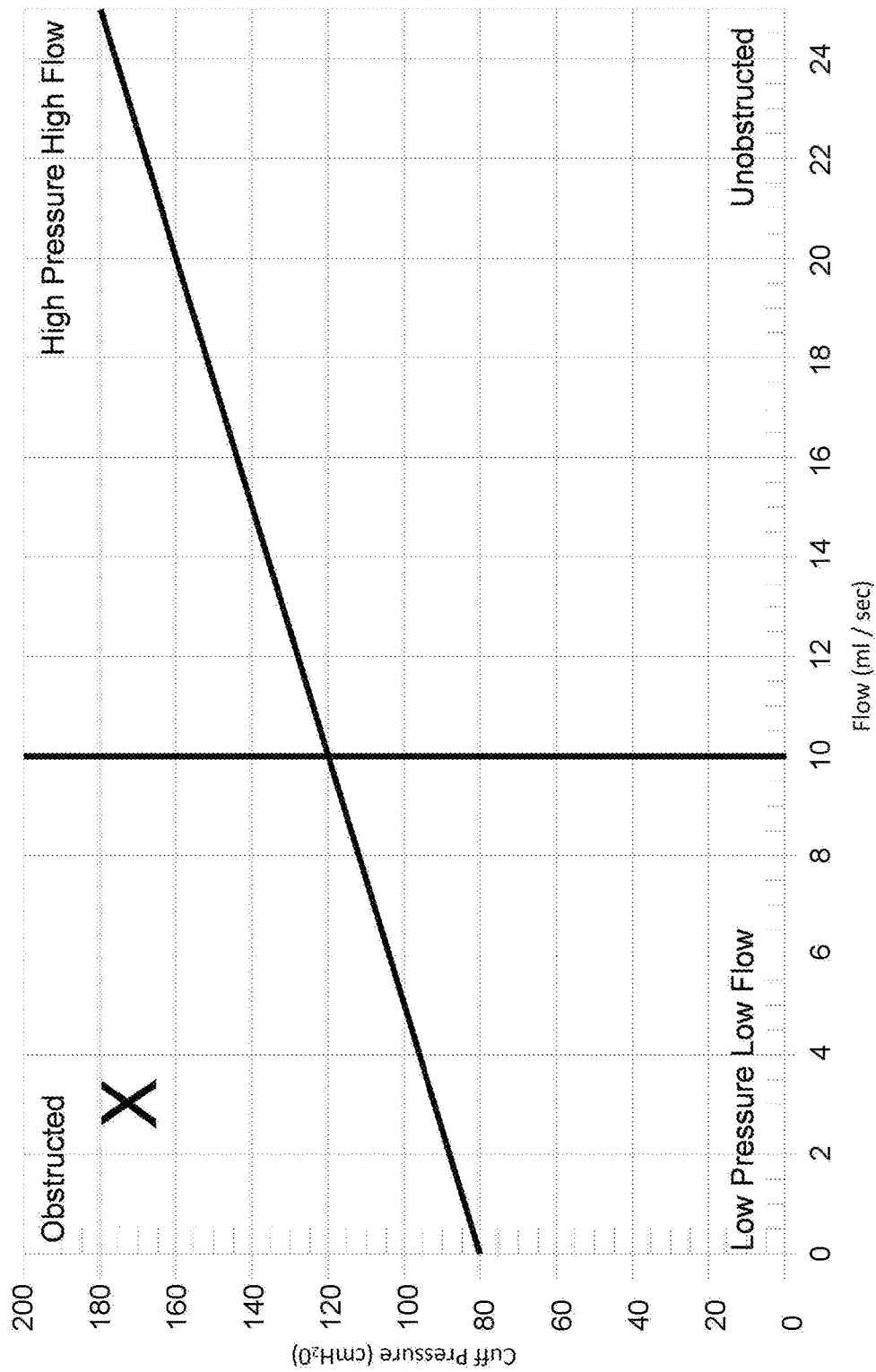
FIGS. 3A and 3B depict illustrative comparative applied pressure-urine flow nomographs for separate subjects.
Figure 3B:
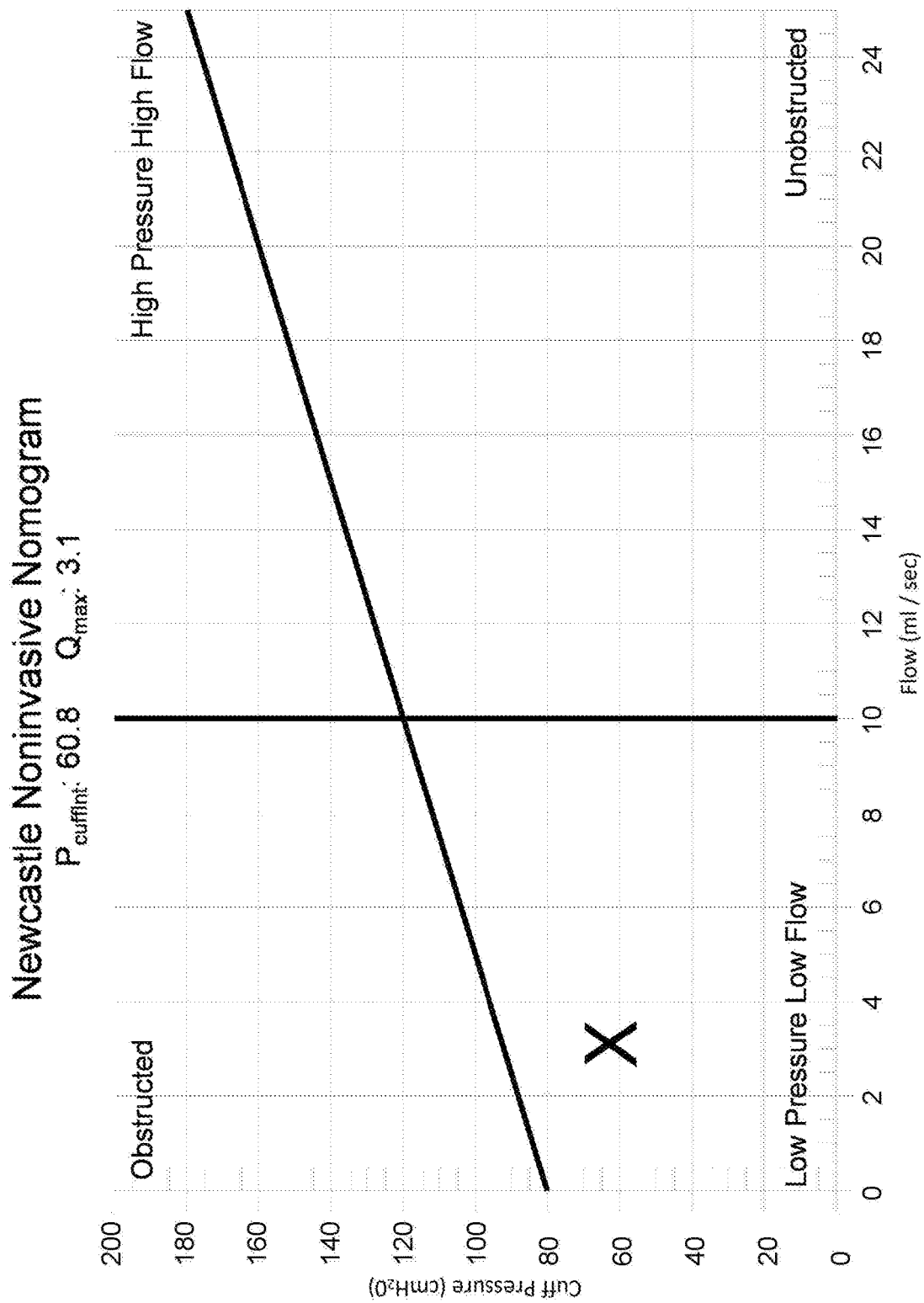
Figure 4:
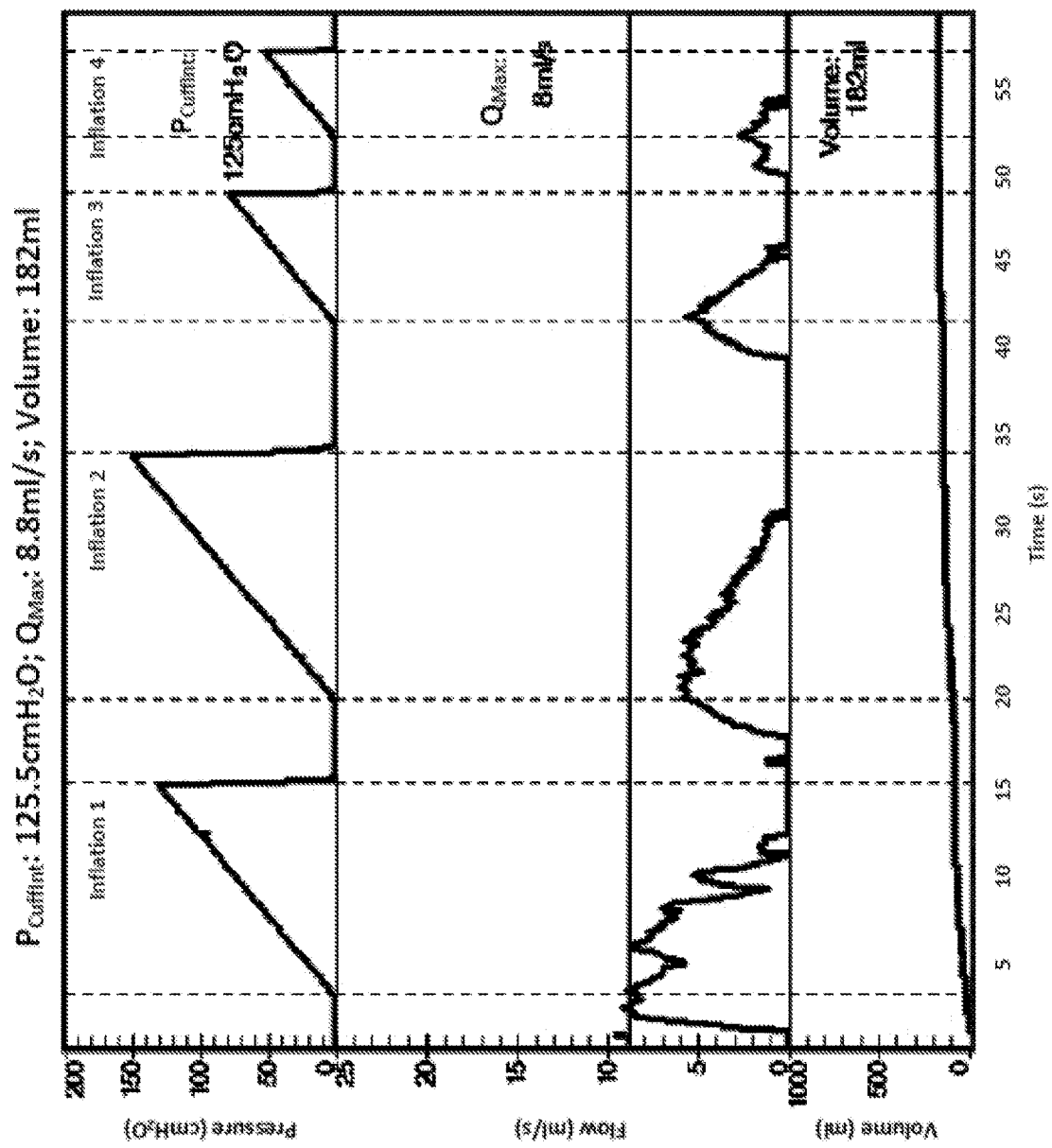
Figure 7:
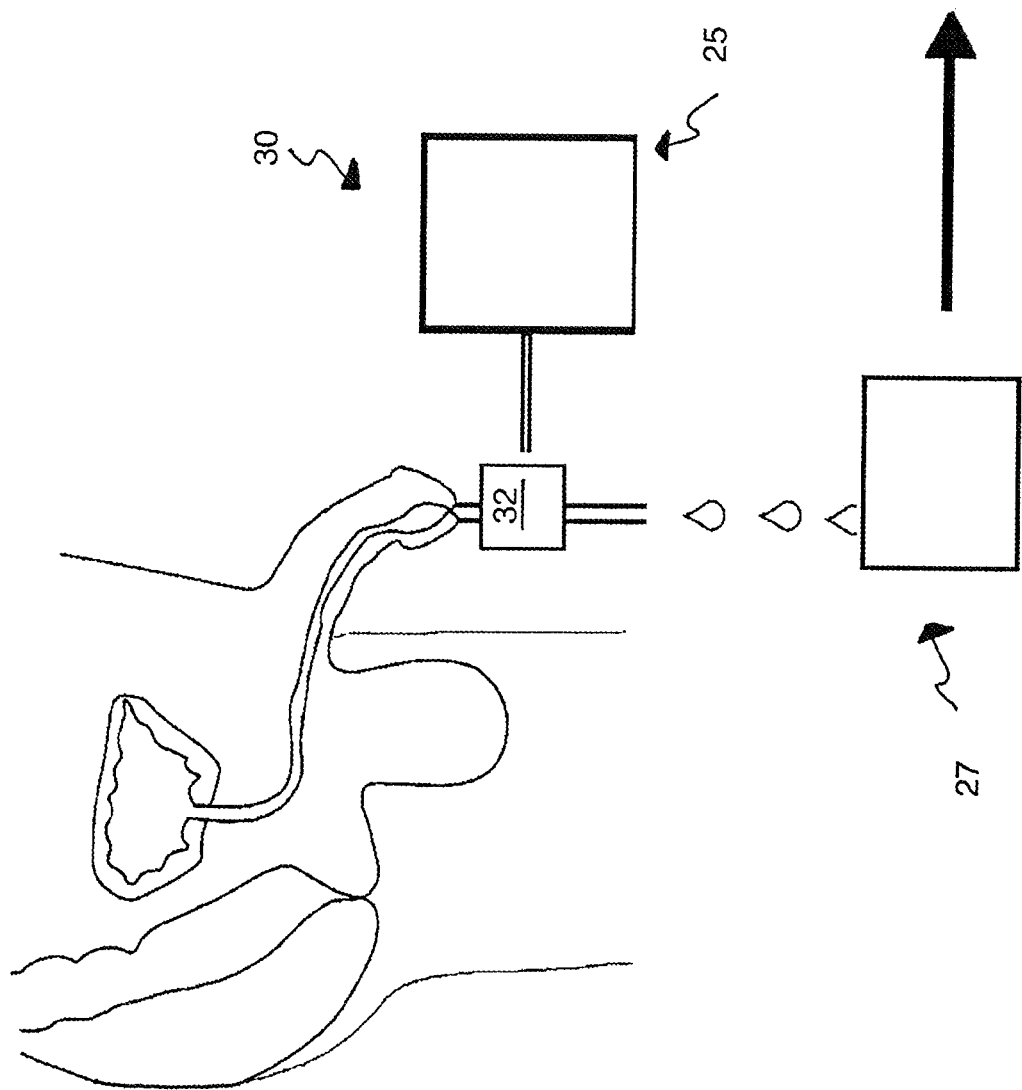

Turning now to the bladder function test system per se, known and adapted test systems are schematically shown, FIGS. 2 & 7 respectively. Inspection and contrast of the schematic test systems yield an intentional, critical point of departure, namely, Applicant abandons penile urethral clamping via application of a penile cuff. While apparatus/systems for pressure application, recording, etc., and apparatus/systems for urine flow rate determination, recording, etc., among other system components and/or features, remain conventional/state-of-the-art, Applicant provides alternate, substitute, surrogate, and/or proxy means for effectuating manipulations to urine discharge flow rates from the bladder via the application of pressure not inconsistent with known bladder function test protocols.

With continued reference to alternate study system 30 of FIG. 7, notionally, means 32 are provided distal or downstream of the urethra as indicated part-and-parcel of the illustrated schematic procedure. Such test system approach offers three distinct advantages: (1) improved patient comfort; (2) simpler placement for medical staff; and, (3) direct compression of the urine stream without implicating penile tissue. Contemplated distal or downstream flow regulation may be accomplished in a variety of ways.

For example, and without limitation, a known or adpated penile clamp may be operatively combined with a standard external male catheter, also known as Texas catheter, condom catheter, or urisheath. Such catheter is traditionally utilized in male patients with incontinence, or urine leakage (see e.g., Hollister Extended Wear Male External Catheter 26-30 mm). The external male catheter is placed around or about the penis so as to form a urine tight seal therewith. The catheter includes a tube extending from a distal end of a condom, the tube commonly terminting at a urine drainage bag. Should a patient leak, urine is passed through the tube and into the drainage bag.

In this scenario, the drainage tube of the external male catheter is equipped or equippable with a pneumatic cuff, with the test subject permitted to void through the external male catheter. As the cuff inflates, pressure is applied to the drainage tube and the urine flow is limited by the applied external pressure applied as per the select bladder function test protocal. Disadvanatges, or at least limitations of this approach are: (1) the large diameter (i.e., approximately 0.375" internal diameter) of the standard catheter drainage tube requires the tube to be physically compressed to affect flow rate; and, (2) the stiffness of the exit tube limits the direct pressure being applied to the urine channel within.

One contemplated, advantageous, non-limiting approach to distal or downstream flow regulation involves using the external male catheter, to make a fluid seal with the exterior surfaces of the penis, and operably unite the catheter, via the drainage tube, to a urodynamic investigation apparatus. An advantageous, non-limiting urodynamic investigation apparatus for indirect union with the penile urethra is depcited in FIG. 8 et seq. As will be subsequently taken up, the contemplated apparatus permits pressure regulated urine flow therethrough in furtherance of bladder function test data acquisition and bladder/lower urinary tract assessment.

A further contemplated, advantageous, non-limiting approach to distal or downstream flow regulation involves provisions for a urodynamic investigation apparatus adapted for cooperative engagement with periurethral tissue of a subject. An advantageous, non-limiting urodynamic investigation apparatus for direct union with the penile urethra is depcited in FIG. 12 et seq. As will be subsequently taken up, the contemplated apparatus permits pressure regulated urine flow therethrough in furtherance of bladder function test data acquisition and bladder/lower urinary tract assessment.

Figure 8:
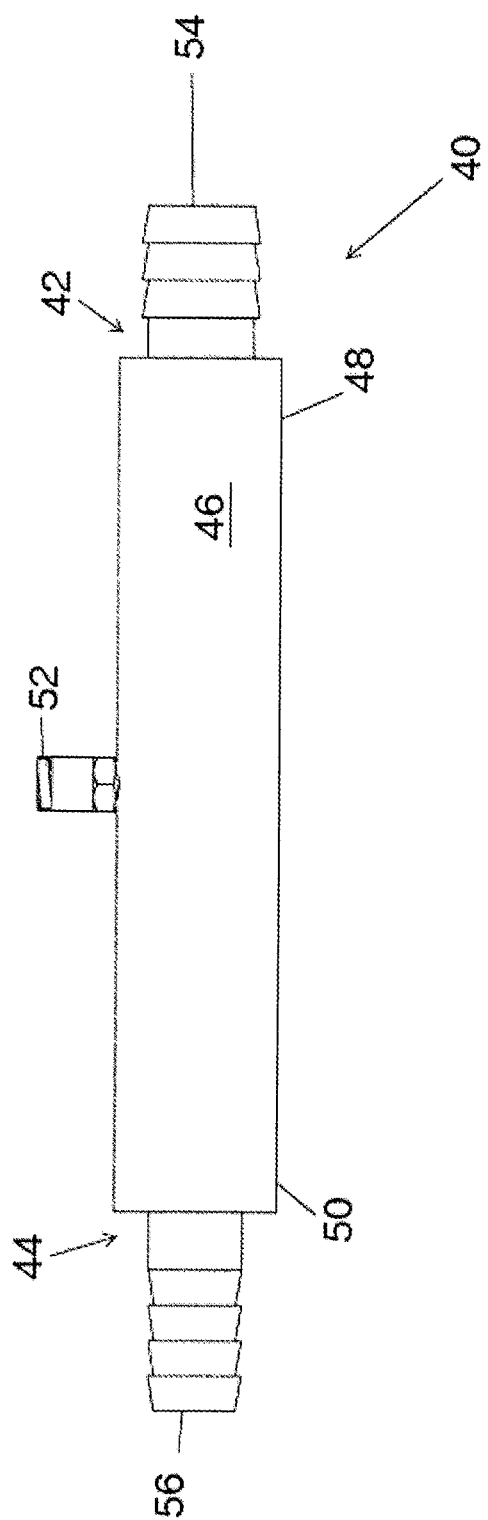
Figure 9:
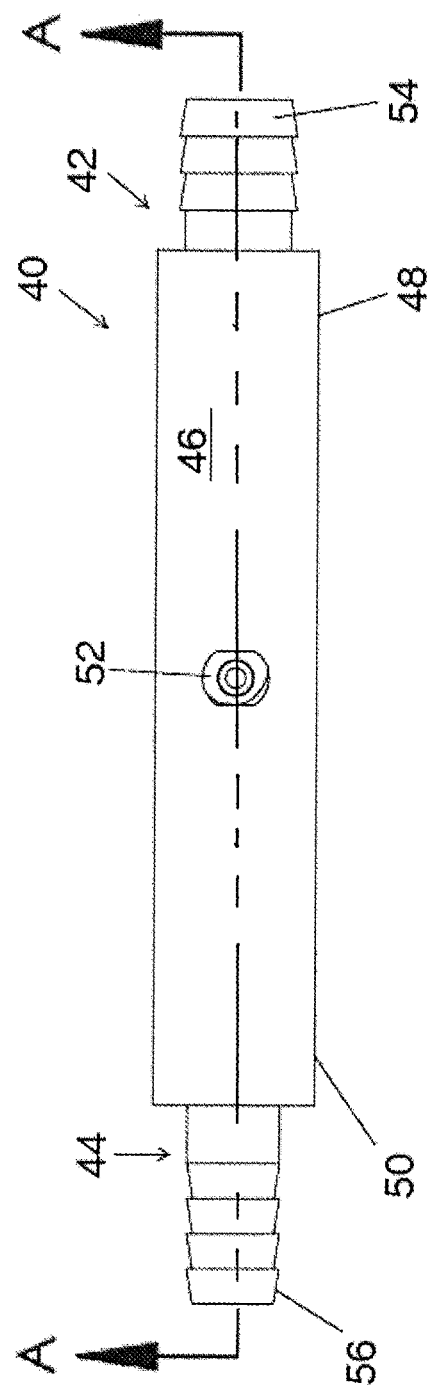
Figure 10:
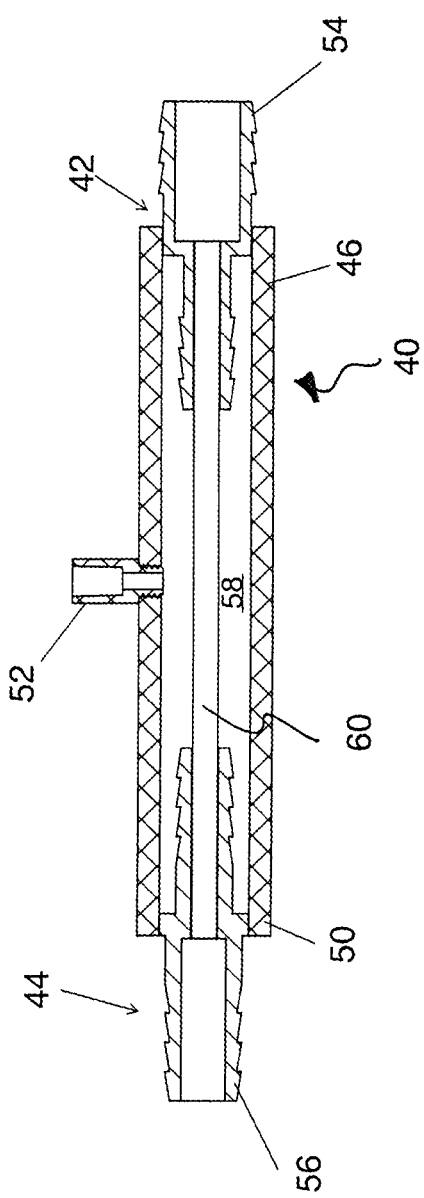
Figure 11:
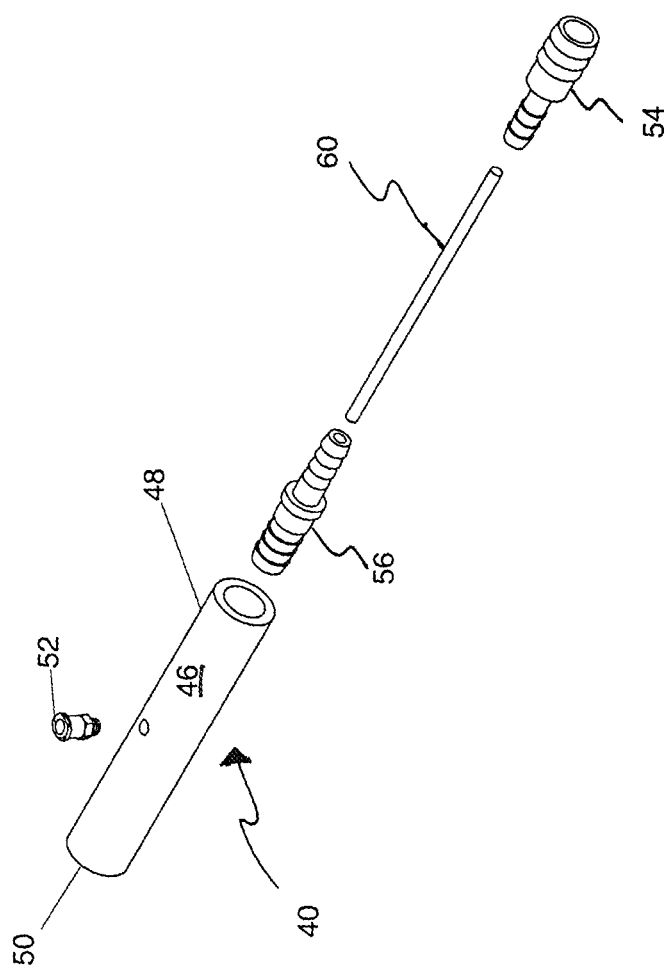
Figure 12:
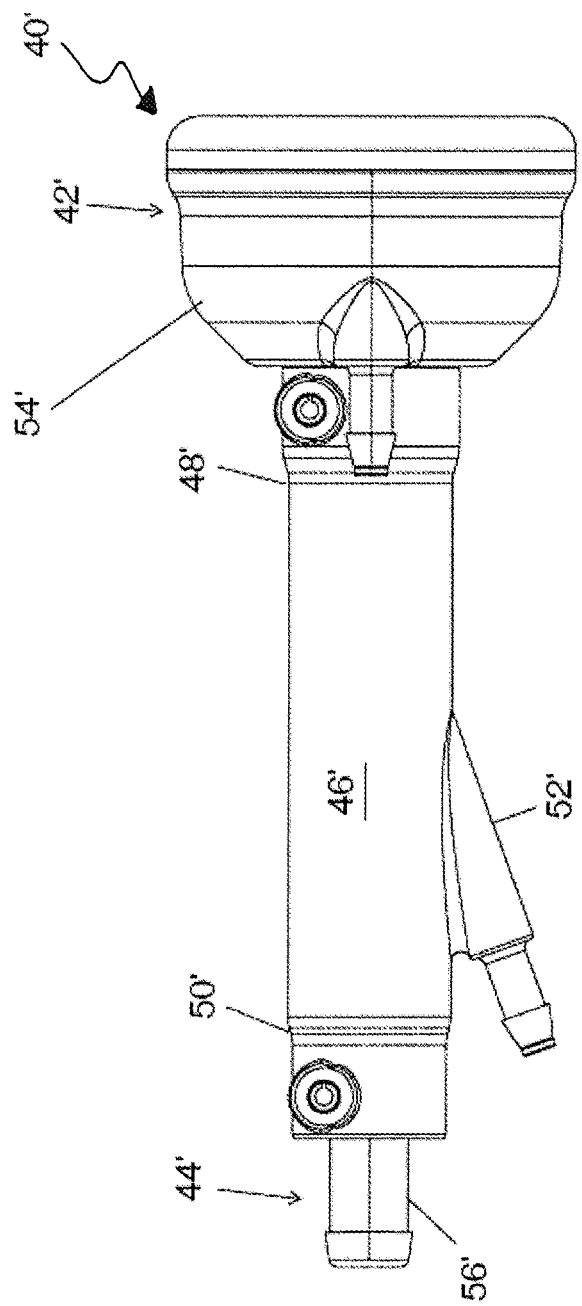
Figure 13:
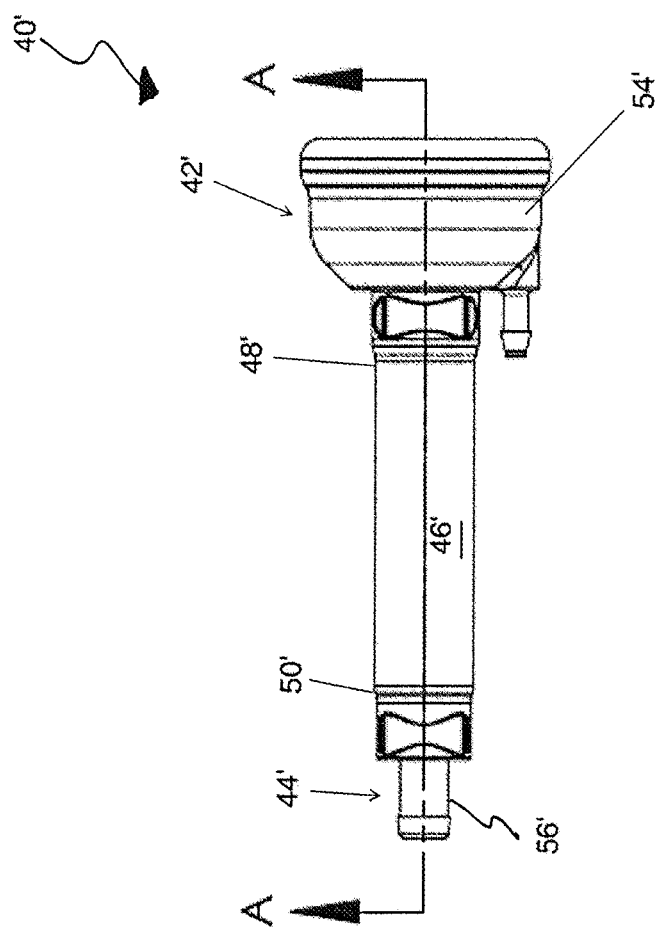
Figure 14:
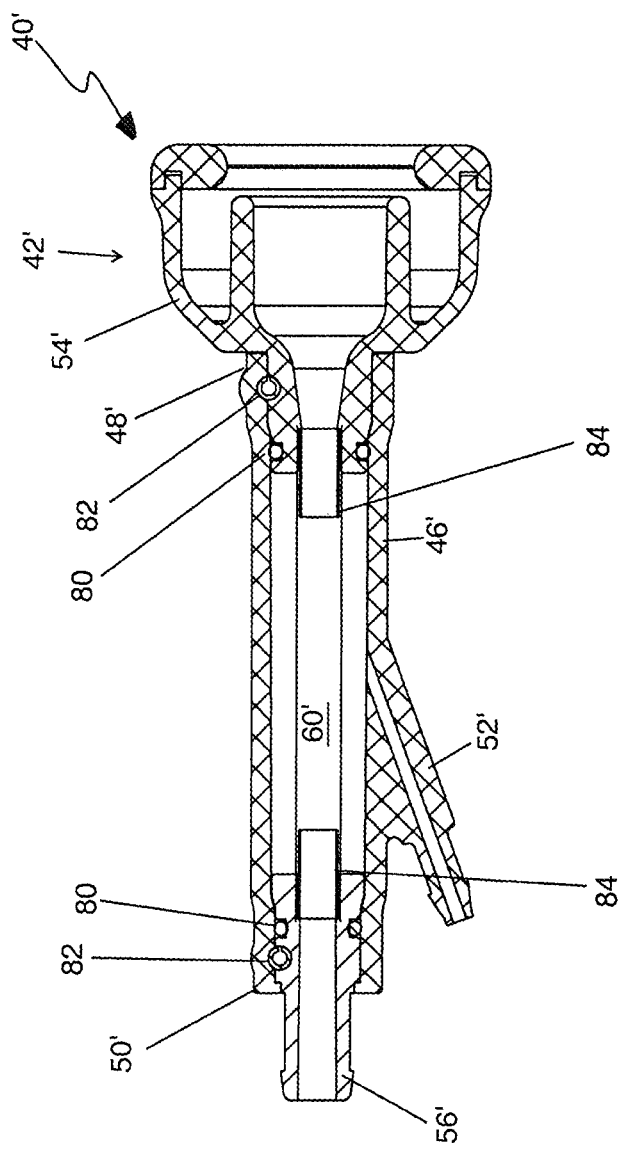
Figure 15:
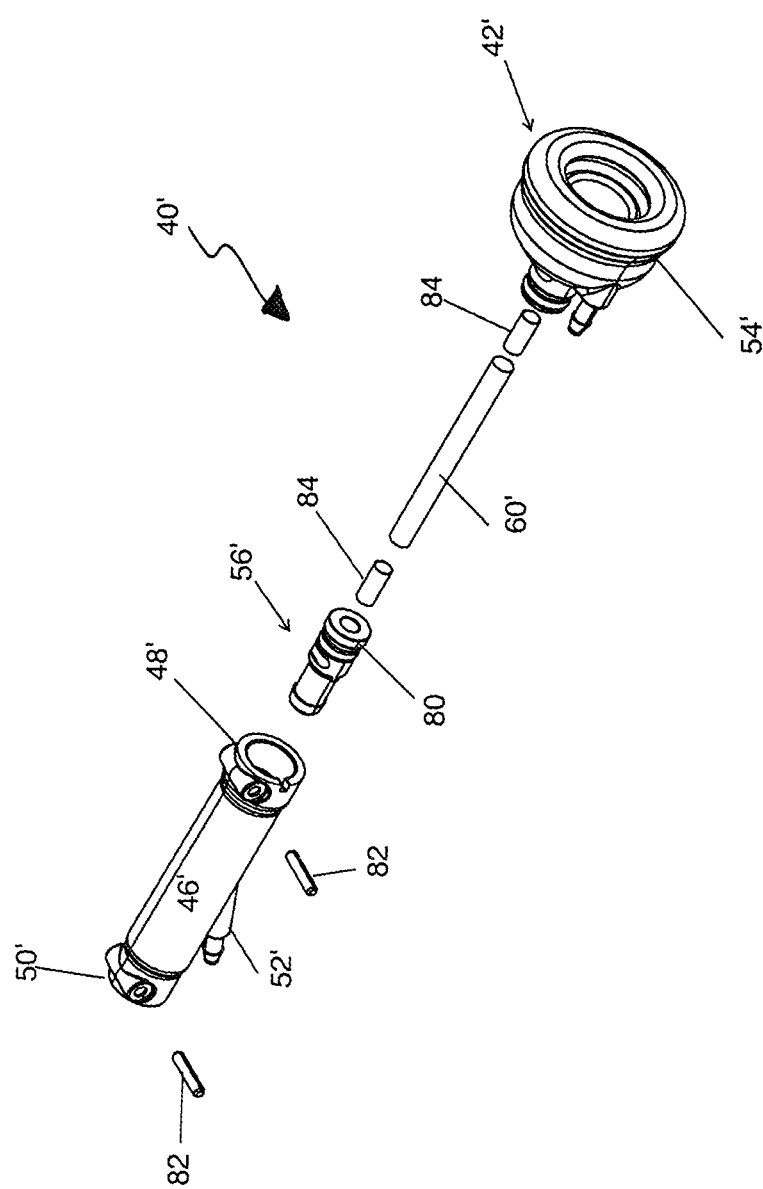

With initial and general reference now to each of FIGS. 8 & 10 on one hand, and FIGS. 12 & 14 on the other hand, there are shown, in elevation and section views, alternate embodiments 40, 40' of a urodynamic investigation apparatus for receipt of urine from a bladder. Apparatus 40, 40' receives voided urine at a urine ingress end 42, 42', and dispatches the received voided urine at a urine egress end 44, 44'.

Apparatus 40, 40' includes a tubular element 46, 46' characterized by opposing first 48, 48' and second 50, 50' end portions, and a port 52, 52', and further includes first 54, 54' and second 56, 56' fittings adapted to be received by opposing first 48, 48' and second 50, 50' end portions of tubular element 46, 46' so as to delimit an apparatus chamber 58, 58'. A sleeve element 60, 60', for select passage of urine there through, is suspended between first 54, 54' and second 56, 56' fittings within chamber 58, 58'. The element may advantageously but not necessarily extend through and exterior of a fitting of the fittings, or through and exterior of each of the fittings. As will be subsequently detailed, the sleeve element has collapsed and open configurations, the collapsed configuration being indicative of a no urine flow condition, the open configuration being indicative of a urine flow condition, with the sleeve element urine flow condition a function of pressure applied to the chamber via the port of the tubular element.

The illustrated apparatuses, or variants thereof, are operably combinable with either or both of a flow rate determination apparatus, for determining rates of urine egress from the sleeve element, and a controllable pressure applying apparatus for selectively applying pressure to the chamber (i.e., establishing a select pressure therein) and to the sleeve element during passage of urine there through. Moreover, bladder function test systems characterized by the contemplated apparatuses, or variants thereof, are not limited to those shown or otherwise disclosed with form generally fitting function relative to either or both of targeted test parameters/sought-after-data and the means/mechanism to process and/or evaluate acquired data.

The tubular element is advantageously, but not necessarily, circular in cross section and of sufficient rigidity to sustain its shape/chamber integrity for/throughout an operative test pressure range of up to about 200 cmH2O. Acrylic or polycarbonite tubing from McMaster Carr (McMaster Carr 8532K15, nominal 0.75"OD) is known to be advantageous in relation to both the FIG. 8 and FIG. 12 embodiments.

The sample port may readily take the form of a tapped fitting (e.g., female luer) through the element sidewall as shown FIG. 8, or may take the form of a branched portion of the element, e.g., a y-extension of the tubular element as shown FIG. 12. In all circumstances, a conventional interface for applying pressure from a pressure source to the chamber of the apparatus via the tubular element is believed suitable.

With particular reference now to FIGS. 8-11, the fittings of the apparatus are sealingly received at and/or by the opposing end portions of the tubular element. Advantageously, but not necessarily, an interface for/between the fittings and the tubular element is characterized by a leak proof seal, for example an impervious adhesive sealant. While "slip" fittings are contemplated and shown, the fittings need not be so limited.

A fitting of one of the first and second fittings may be adapted for operative union with a urine egress routing tube, or the fitting may be adapted for operative union with flowrate determination apparatus. With one fitting so adapted, the other fitting is advantageously adapted for operative union with an external catheter.

With particular reference now to FIGS. 12-15, fittings 54', 56' of apparatus 40' are, as the FIG. 8 embodiment, sealingly received at and/or by the opposing end portions 48', 50' of the tubular element 46'. Advantageously, but not necessarily, an interface for/between the fittings and the tubular element is characterized by a leak proof seal, more particularly as shown, the interface may be advantageously but not necessarily characterized by an O-ring 80. Moreover, the interface is further characterized by a mechanical fastener, more particularly as shown, the interface may be advantageously but not necessarily characterized by a slotted spring pin 82.

A fitting of one of the first and second fittings may be adapted for operative union with a urine egress routing tube, or the fitting may be adapted for operative union with flowrate determination apparatus in keeping with the FIG. 8 embodiment. With one fitting so adapted, the other fitting is advantageously adapted for cooperative engagement with periurethral tissue, or adapted to receive periurethral tissue therein as the case may be. In contradistinction the apparatus of FIG. 8, the instant apparatus is directly linked to the penile urethra via a urethra engaging device (UED), advantageously, but not necessarily, a UED as disclosed by Kron et al. via U.S. Pat. No. 9,277,884, and/or in one or more patent family members having origins therein, each of which are incorporated herein by reference in their entireties.

Sleeve element 60' is generally suspended within chamber 58' of apparatus 40' via fittings 54', 56' or adaptations thereof. More particularly, the sleeve element extends between each of the fittings via an indirect affixation or anchoring with respect thereto (FIG. 14), as by means of anchors in the form of couplings 84. Notionally, the sleeve element is a fluid extension of the urethra (i.e., it is in fluid communication therewith, as by direct means, e.g., a UED or the like (FIG. 12), as opposed to indirect means, e.g., a urine drainage line of an external catheter (FIG. 8 embodiment)).

A desirable and advantageous property of/for the sleeve element is, but is not necessarily limited to, compliance. The sleeve element (i.e., the portion spanning the anchored ends thereof), in an "out-of-the-box" state or condition (i.e., static state), has a minimal cross sectional area, with a typical void event essentially opening and filling the sleeve element and passing urine there through, an "active" lumen for urine passage thereby delimited. Application of pressure to the chamber via the port of the tubular element of the apparatus results in a sleeve element response, namely, a collapsing of the lumen with a commensurate altering of the urine flow rate of the urine passing there through.

For example, and without limitation, the sleeve element (i.e., urine pathway) advantagesouly comprises a thermoplastic, more particularly, but not necessarily, the sleeve element comprises a heat shrink material, more particularly still, a heat shrink material from Nordson Medical, Colorado, USA, namely Nordson Part Number 103-0042. This material has an expanded internal diameter of about 0.140" and a nominal wall thickness of 0.00025". The sleeve element advantageously has highly compliant walls, a resting/static closed configuration (i.e., flat/near flat condition), and an active condition characterized by an expanded diamater (e.g., up to about to 0.140") owing to urine flow passage therethrough.

Beyond the aforementioned advantages of the instant urodynamic investigation apparatus, it is again emphasized that a urine routing tube, e.g., conventional 0.125"-0.250" ID tygon tubing, may be readiliy linked to the urine egress portion of the apparatus via the fitting thereof. This allows for two options to more accurately measure urine flow rate and total voided volume.

First, the distal end of the routing tubing can be placed in close proximity to a urine scale so that the urine is routed to the scale without loss. The distal end of the routing tubing can also be made to float, so that it can be placed directly into the urine beaker on the scale and sit above the voided urine. This can be accomplished, for example, by attaching the distal end of the routing to a small styrofoam float or the like which sits in the urine beaker.

Second, the routing tubing can be connected to a non-contact liquid flow meter, for example and without limitation, the UF32210 Clamp-On Ultrasonic Flow Sensor by Strain Measurement Devices. The flow sensor non-invasively measures urine flow in real-time, allowing the urine to still be routed to the scale for calculation refinement, or the urine can be routed directly to a toilet for direct disposal.

Thus, the instant apparatus, in the context of an improved bladder function test/test set up, overcomes shortcomings of traditional urine flow rate determination via urine free flow onto a supported urine scale wherein: (1) urine may not land on the scale and is thus not calculated into flow rate and voided volume; (2) the force of the urine hitting the scale may result in pertubations of the weight of urine on the scale and result in "noise" in the flow calculation; and, (3) the time for the urine to travel to the scale results in a delay in relationship between pressure and flow.

What has been described and depicted herein are preferred, non-limiting embodiments of Applicant's subject matter, along with some application contexts. Since the elements of the system and/or structures of the assemblies, subassemblies, and/or mechanisms disclosed herein may be embodied in other specific forms without departing from the spirit or general characteristics thereof, some of which forms have been indicated, the embodiments described and depicted herein/with are to be considered in all respects illustrative and not restrictive. Moreover, while nominal operational steps or sequences and/or a protocol have been set forth, and to some degree alternate work pieces and systems, assemblies, etc. with regard thereto referenced, contemplated sequences/protocols are not so limited. Accordingly, the scope of the subject invention is as defined in the language of the appended claims, and includes not insubstantial equivalents thereto.

That which is claimed:

1. An improved urodynamic pressure profiling method comprising the steps of:
   a. applying a series of positive pressures to a lumen carrying urine discharge from a bladder during a void event without terminating urine flow through the lumen;
   b. determining a urine flow rate resulting from applied pressures of said series of applied pressures; and,
   c. ascertaining, via an assessment of applied pressures and resulting urine flow rates of said series of applied pressures, either or both of an applied pressure corresponding to a no flow urine condition and a maximum urine discharge flow rate.

2. The method of claim 1 wherein the applied pressures are within a pressure range of about 30 to 60 centimeters of water.

3. The method of claim 1 wherein the applied pressures of said series of applied pressures are in 10 centimeters of water increments.

4. The method of claim 1 further comprising measuring and recording abdominal surface electromyography concurrent to pressure application to the lumen carrying urine discharge from the bladder.

5. The method of claim 1 wherein said series of applied pressures is a first series of applied pressures characterized by an incremental progression of applied pressure.

6. The method of claim 1 wherein said series of applied pressures is a first series of applied pressures characterized by an incremental progression of applied pressure, said incremental progression of applied pressure ending at about 60 centimeters of water.

7. The method of claim 1 wherein said series of applied pressures comprises a first series of applied pressures and a second series of applied pressures, each series of applied pressures characterized by an incremental linear progression of applied pressure.

8. The method of claim 1 wherein said series of applied pressures comprises two series of applied pressures characterized by an incremental progression of applied pressure wherein periods of pressure relief follow each series of applied pressures of said series of applied pressures.

9. An improved urodynamic pressure profiling method comprising the steps of:
   a. applying a series of positive pressures to a lumen of an extracorporeal device carrying urine discharge from a bladder during a void event without terminating urine flow through the lumen wherein the extracorporeal device comprises a pressure chamber;
   b. determining a urine flow rate resulting from applied pressure of said series of applied pressures; and,
   c. ascertaining, via an assessment of applied pressures and resulting urine flow rates of said series of applied pressures, either or both of an applied pressure corresponding to a no flow urine condition and a maximum urine discharge flow rate.

10. The method of claim 9 wherein the applied pressures are within a pressure range of about 0 to 60 centimeters of water.

11. The method of claim 9 wherein the applied pressures are within a pressure range of about 30 to 60 centimeters of water.

12. The method of claim 9 wherein the applied pressures of said series of applied pressures are in 10 centimeters of water increments.

13. The method of claim 9 further comprising measuring and recording abdominal surface electromyography concurrent to pressure application to the lumen carrying urine discharge from the bladder.

14. The method of claim 9 wherein said extracorporeal device includes a fitting adapted for receipt of periurethral tissue.

15. The method of claim 9 said extracorporeal device is characterized by a urethral engagement element for engagement with a penile urethra.

16. The method of claim 9 wherein said series of applied pressures is a first series of applied pressures characterized by an incremental progression of applied pressure.

17. The method of claim 9 wherein said series of applied pressures is a first series of applied pressures characterized by an incremental progression of applied pressure, said incremental progression of applied pressure starting at about 0 centimeters of water and ending at about 60 centimeters of water.

18. The method of claim 9 wherein said series of applied pressures comprises a first series of applied pressures and a second series of applied pressures, each series of applied pressures characterized by an incremental linear progression of applied pressure.

19. The method of claim 1 wherein said series of applied pressures comprises two series of applied pressures characterized by an incremental progression of applied pressures wherein periods of pressure relief follow each series of applied pressure of said series of applied pressures.

20. An improved urodynamic pressure profiling method comprising the steps of:
   a. applying a first pressure to a lumen of an extracorporeal device carrying urine discharge from a bladder during a void event, without terminating urine flow through the lumen during the void event, and determining a urine flow rate resulting from the first applied pressure;
   b. applying a second pressure to the lumen of an extracorporeal device carrying urine discharge from the bladder during the void event, without terminating urine flow through the lumen during the void event, and determining a urine flow rate resulting from the second applied pressure, the second pressure greater or less than the first pressure by a select pressure increment;

c. applying a third pressure to the lumen of an extracorporeal device carrying urine discharge from the bladder during the void event, without terminating urine flow through the lumen during the void event, and determining a urine flow rate resulting from the third applied pressure, the third pressure greater or less than the second pressure by a select pressure increment; and, d. ascertaining, via an assessment of applied pressures and resulting flow rates of the applied pressures, either or both of an applied pressure corresponding to a no flow urine condition and a maximum urine discharge flow rate.

21. The method of claim 20 wherein the applied pressures are within a pressure range of about 0 to 60 centimeters of water.

22. The method of claim 20 wherein the applied pressures are within a pressure range of about 30 to 60 centimeters of water.

23. The method of claim 20 wherein the applied pressures of said series of applied pressures are in 10 centimeters of water increments.

24. The method of claim 20 further comprising measuring and recording abdominal surface electromyography concurrent to pressure application to the lumen carrying urine discharge from the bladder.

25. The method of claim 20 wherein said extracorporeal device includes a fitting adapted for receipt of periurethral tissue.

26. The method of claim 20 said extracorporeal device is characterized by a urethral engagement element for engagement with a penile urethra.

27. The method of claim 20 wherein said first, second and third applied pressures comprise a first series of applied pressures wherein a period of pressure relief follows said first series of applied pressures.

28. The method of claim 20 wherein said first, second and third applied pressures comprise a first series of applied pressures, a period of pressure relief follows said first series of applied pressures and a second series of applied pressures is thereafter applied to the lumen carrying urine discharge from a bladder during a void event.

* * * * *